United States Patent
Miki et al.

(10) Patent No.: US 11,421,043 B2
(45) Date of Patent: Aug. 23, 2022

(54) METHOD FOR PRODUCING SIEVED LOW-SUBSTITUTED HYDROXYPROPYL CELLULOSE

(71) Applicant: Shin-Etsu Chemical Co., Ltd., Tokyo (JP)

(72) Inventors: Kentaro Miki, Niigata (JP); Akiko Tsuchida, Niigata (JP); Akira Kitamura, Niigata (JP); Yasuyuki Hirama, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/000,836

(22) Filed: Aug. 24, 2020

(65) Prior Publication Data
US 2021/0061926 A1 Mar. 4, 2021

(30) Foreign Application Priority Data
Aug. 27, 2019 (JP) .............................. JP2019-154552

(51) Int. Cl.
*C08B 11/20* (2006.01)
(52) U.S. Cl.
CPC .................... *C08B 11/20* (2013.01)
(58) Field of Classification Search
CPC ....................................................... C08B 11/20
See application file for complete search history.

(56) References Cited

U.S. PATENT DOCUMENTS

| | | | | |
|---|---|---|---|---|
| 10,513,565 B2* | 12/2019 | Hirama | ..................... | C08B 3/14 |
| 2002/0058714 A1* | 5/2002 | Maruyama | .............. | C08L 1/284 |
| | | | | 514/781 |
| 2018/0049990 A1* | 2/2018 | Hirama | ................... | A61K 47/38 |
| 2018/0100027 A1* | 4/2018 | Hirama | ..................... | C08B 3/08 |
| 2018/0100029 A1* | 4/2018 | Hirama | ................ | A61K 9/2095 |

FOREIGN PATENT DOCUMENTS

EP 3308775 A1 4/2018
JP H07324101 12/1995

OTHER PUBLICATIONS

Merkus et al. "Particle Size Measurements: Fundamentals, Practice, Quality" In: "Particle Size Measurements" pp. 224-229 {Jan. 20, 2009} (Year: 2009).*

(Continued)

*Primary Examiner* — Isaac Shomer
(74) *Attorney, Agent, or Firm* — Myers Bigel, P.A.

(57) ABSTRACT

There is provides a method for producing sieved low-substituted hydroxypropyl cellulose (L-HPC) at improved yield, while maintaining flowability and tablet properties. More specifically, there is provided a method for producing sieved L-HPC including a first sieving step of sieving L-HPC having a hydroxypropoxy group content of 5 to 16% by mass with a sieving shaker with horizontal movement of a sieve surface to obtain first sieve-residual L-HPC and first sieve-passed L-HPC, a second sieving step of sieving the first sieve-residual L-HPC with a sieving shaker with vertical movement of a sieve surface to obtain second sieve-residual L-HPC and second sieve-passed L-HPC, and a step of combining the first sieve-passed L-HPC and the second sieve-residual L-HPC to obtain the sieved L-HPC.

8 Claims, 1 Drawing Sheet

(56) References Cited

OTHER PUBLICATIONS

Extended European Search Report corresponding to European Patent Application No. 20192380.2 (9 pages) (dated Jan. 25, 2021).
Merkus et al. "Particle Size Measurements: Fundamentals, Practice, Quality" In: "Particle Size Measurements" pp. 224-229 (Jan. 20, 2009).

* cited by examiner

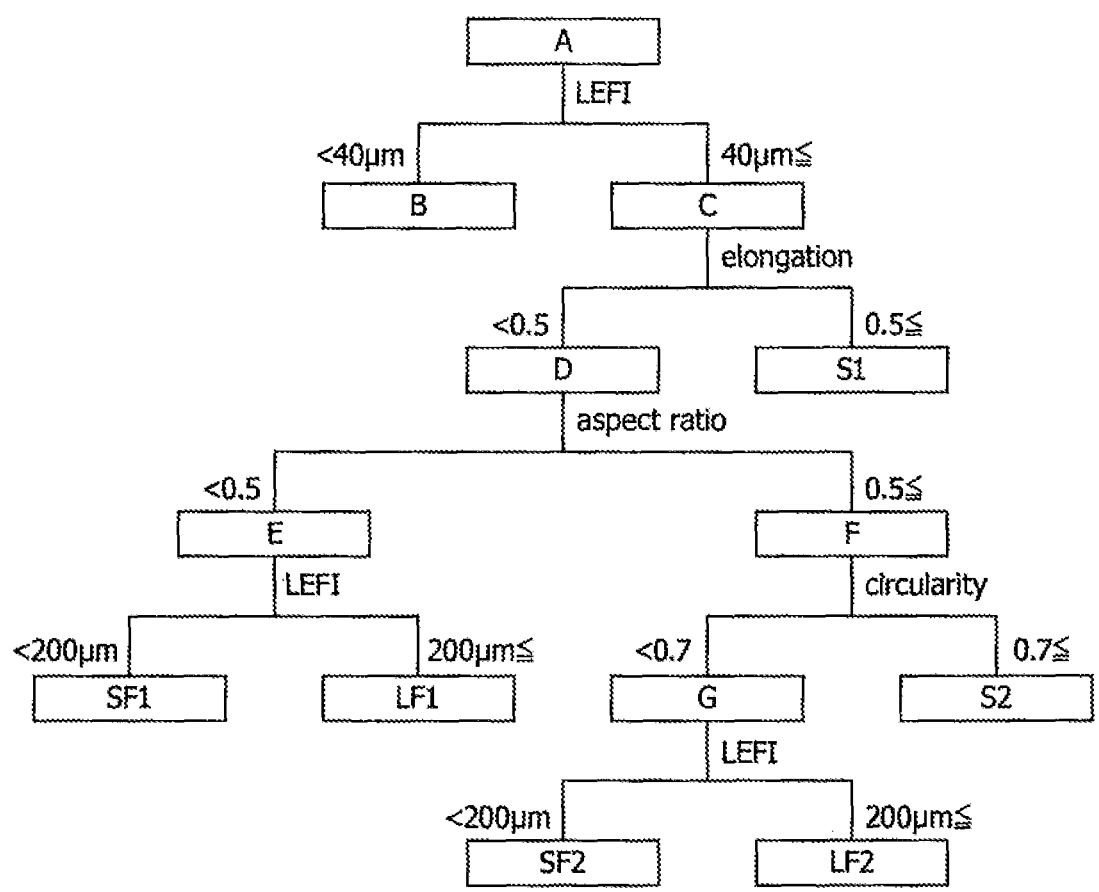

METHOD FOR PRODUCING SIEVED LOW-SUBSTITUTED HYDROXYPROPYL CELLULOSE

CROSS-REFERENCE TO RELATED APPLICATION

This U.S. nonprovisional application claims priority to Japanese Application No. 2019-154552 filed Aug. 27, 2019, the entire contents of which are incorporated herein by reference.

BACKGROUND OF THE INVENTION

1. Field of the Invention

The invention relates to a method for producing sieved low-substituted hydroxypropyl cellulose at improved yield.

2. Related Art

A solid preparation disintegrates through water absorption and water swell of the disintegrant contained therein. Examples of the disintegrant include low-substituted hydroxypropyl cellulose (hereinafter, also referred to as "L-HPC"), carboxymethylcellulose, carboxymethylcellulose calcium, starch and starch derivatives. Among them, L-HPC is widely used as a nonionic disintegrant.

The particle size distributions and particle shapes of L-HPC are variable depending on applications. However, since insufficiently pulverized coarse fibrous particles reduce flowability and deteriorate uniform mixing with the active ingredient as well as weight uniformity between tablets, L-HPC is commonly produced by sieving after pulverization (JP 07-324101A)

SUMMARY OF THE INVENTION

When the sieving is carried out by horizontally moving the sieve surface on which L-HPC is placed, for example, the faction to be removed contains not a small amount of L-HPC having the targeted particle size distribution and particle shape. Thus, there is room for improvement in terms of yield.

In view of the above circumstances, an object of the invention is to provide a method for producing sieved L-HPC at improved yield, while maintaining the same flowability and tablet properties as those of L-HPC obtained by a conventional sieving method.

As a result of intensive studies to achieve the object, the inventors have found that sieved L-HPC can be produced at high yield, while maintaining good flowability and tablet properties, by subjecting the fraction conventionally removed by sieving with horizontal movement of a sieve surface, to further sieving with a sieve with vertical movement of a sieve surface; and have completed the invention.

In one aspect of the invention, there is provided a method for producing sieved low-substituted hydroxypropyl cellulose comprising:

a first sieving step of sieving low-substituted hydroxypropyl cellulose having a hydroxypropoxy group content of 5 to 16% by weight with a sieving shaker with horizontal movement of a sieve surface to obtain first sieve-residual low-substituted hydroxypropyl cellulose and first sieve-passed low-substituted hydroxypropyl cellulose, a second sieving step of sieving the first sieve-residual low-substituted hydroxypropyl cellulose with a sieving shaker with vertical movement of a sieve surface to obtain second sieve-residual low-substituted hydroxypropyl cellulose and second sieve-passed low substituted hydroxypropyl cellulose, and a step of combining the first sieve-passed low-substituted hydroxypropyl cellulose and the second sieve-residual low-substituted hydroxypropyl cellulose to obtain the sieved low-substituted hydroxypropyl cellulose.

According to the invention, sieved L-HPC can be produced at enhanced yield, while maintaining the same good flowability and tablet properties as those of L-HPC obtained in a conventional sieving method.

BRIEF DESCRIPTION OF THE DRAWINGS

FIG. 1 shows a flow chart of dividing "all particles" of L-HPC into four types of particles: "fine particles", "long fibrous particles (LF1 and LF2)", "short fibrous particles (SF1 and SF2)", and "spherical particles (S1 and S2)".

DETAILED DESCRIPTION OF THE PREFERRED EMBODIMENTS (1) Methods for Classifying L-HPC Particles In this specification, L-HPC particles are divided into four types of particles: "long fibrous particles", "short fibrous particles", "spherical particles" and "fine particles". FIG. 1 shows a flowchart summarizing the method of dividing "all particles" of L-HPC into four types of particles: "fine particles", "long fibrous particles (LF1 and LF2)", "short fibrous particles (SF1 and SF2)" and "spherical particles (S1 and S2)".

A volume fraction of each type of L-HPC particles can be calculated by measuring the shape parameters such as a length of fiber (LEFI), a diameter of fiber (DIFI), an elongation, an aspect ratio and a circularity based on a dynamic-image analysis. The dynamic image analysis is a method in which images of particles dispersed in a fluid such as a gas or a solvent are continuously photographed and are binarized and analyzed to obtain a particle diameter or a particle shape. The analysis may be performed by using, for example, a dynamic-image analysis type particle diameter distribution analyzer, QICPIC/R16 (manufactured by Sympatec GmbH).

All particles A are divided into particles C having a length of fiber (LEFI) of 40 µm or more and fine particles B having a length of fiber of less than 40 µm. The LEFI is defined as the length of the longest direct path that connects the ends of the particle within the contour of the particle. A QICPIC/R16 equipped with an M7 lens has a detection limit of 4.7 µm, and thus fails to detect a particle of an LEFI of less than 4.7 µm. However, the volume of the particles having an LEFI of less than 4.7 µm is extremely small relative to that of all particles of L-HPC, so that it is negligible for the purposes of the invention.

The particles C having an LEFI of 40 µm or more are divided into first spherical particles (S1) having an elongation of 0.5 or more and particles D having an elongation of less than 0.5, wherein the elongation is a ratio (DIFI/LEFI) of a diameter of the fiber (DIFI) to LEFI of the particle. The DIFI is defined as the minor diameter of a particle, and is calculated by dividing the projection area of the particle by the sum of all lengths of the fiber branches of the particle.

The particles D having an LEFI of 40 µm or more and an elongation of less than 0.5 are divided into particles E having an aspect ratio of less than 0.5 and particles F having an aspect ratio of 0.5 or more, wherein the aspect ratio is a ratio (Fmin/Fmax) of the minimum Feret diameter (Fmin) to the maximum Feret diameter (Fmax). Each particle has an aspect ratio of more than 0 and not more than 1. The Feret diameter is the distance between two parallel tangent lines that put the particle therebetween. The minimum Feret diameter (Fmin) is a minimum distance between pairs of tangent lines to the particle in consideration of all possible orientations by changing the direction from 0° to 180°, and the maximum Feret diameter (Fmax) is the largest distance between pairs of tangent lines to the particle in consideration of all possible orientations by changing the direction from 0° to 180°.

The fibrous particles E having an LEFI of 40 μm or more, and an elongation of less than 0.5, and an aspect ratio of less than 0.5 are divided into first long fibrous particles (LF1) having an LEFI of 200 μm or more and first short fibrous particles (SF1) having an LEFI of less than 200 μm.

The particles F having an LEFI of 40 μm or more, and an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_p$) of the particle to the real perimeter ($P_{real}$) of the particle, and is defined in the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywod diameter.

$$\text{Circularity} = P_{EQPC}/P_{real} = 2\sqrt{\pi \cdot A_p}/P_{real}$$

The fibrous particles G having an LEFI of 40 μm or more, an elongation of less than 0.5, an aspect ratio of 0.5 or more, and a circularity of less than 0.7 are divided into second long fibrous particles (LF2) having an LEFI of 200 μm or more and second short fibrous particles (SF2) having an LEFI of less than 200 μm.

The volume ($V_m$) of the fine particles of L-HPC may be calculated by the following equation where each fine particle is assumed to be a sphere having a diameter of EQPC.

$$V_m = (\pi/6) \times (EQPC)^3 \times N_m,$$

wherein $N_m$ is the number of fine particles in a sample, and EQPC is a median EQPC corresponding to the 50% cumulative value on a number-based cumulative particle diameter distribution curve of fine particles.

In the specification, particles having an LEFI of 40 μm or more, which are particles other than the fine particles having an LEFI of less than 40 μm among all the particles, are divided into "long fiber particles", "short fiber particles" and "spherical particles", which are distinguished from each other. This division or classification is based on the above shape parameters of particles including LEFI, an elongation, an aspect ratio and a circularity.

<Long Fibrous Particles>

Particles satisfying the following definition of LF1 or LF2 are divided into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of L-HPC may be calculated by the following equation wherein each long fibrous particle is assumed to be a cylindrical column having a bottom diameter of DIFI and a height of LEFI.

$$V_{LF} = (\pi/4) \times (DIFI)^2 \times (LEFI) \times N_{LF},$$

wherein $N_{LF}$ is the number of long fibrous particles in the sample, DIFI is a median DIFI corresponding to the 50% cumulative value on the number-based cumulative particle diameter distribution curve of long fibrous particles, and LEFI is a median LEFI corresponding to the 50% cumulative value on the number-based cumulative particle diameter distribution curve of long fibrous particles.

The volume of particles satisfying the definition of LF1 and the volume of particles satisfying the definition of LF2 are calculated in accordance with the above equation, respectively, and a sum of these volumes means the volume of the long fibrous particles of L-HPC.

<Short Fibrous Particles>

Particles satisfying the following definition of SF1 or SF2 are classified into "short fibrous particles".

SF1: particles having an elongation of less than 0.5, an aspect ratio of less than 0.5, and an LEFI (length of fiber) of 40 μm or more and less than 200 μm, and SF2: particles having an elongation of less than 0.5, an aspect ratio of 0.5 or more, a circularity of less than 0.7, and an LEFI (length of fiber) of 40 μm or more and less than 200 μm.

The volume ($V_{SF}$) of the short fibrous particles of L-HPC may be calculated by the following equation where each short fibrous particle is assumed to be a cylindrical column having a bottom diameter of DIFI and a height of LEFI, in the same manner as for the above long fibrous particles.

$$V_{SF} = (\pi/4) \times (DIFI)^2 \times (LEFI) \times N_{SF},$$

wherein $N_{SF}$ is the number of short fibrous particles in the sample, DIFI is a median DIFI corresponding to the 50% cumulative value on the number-based cumulative particle diameter distribution curve of short fibrous particles, and LEFI is a median LEFI corresponding to the 50% cumulative value on the number-based cumulative particle diameter distribution curve of short fibrous particles.

The volume of particles satisfying the definition of SF1 and the volume of particles satisfying the definition of SF2 are calculated in accordance with the above equation, respectively, and a sum of these volumes means the volume of the short fibrous particles of L-HPC.

<Spherical Particles>

Particles satisfying the definition S1 or S2 is classified into "spherical particles".

S1: particles having an LEFI (length of fiber) of 40 μm or more and an elongation of 0.5 or more, and S2: particles having an LEFI (length of fiber) of 40 μm or more, an elongation of less than 0.5, an aspect ratio of 0.5 or more, and a circularity of 0.7 or more.

The volume ($V_S$) of the spherical particles of L-HPC may be calculated by the following equation, wherein each spherical particle is assumed to be a sphere having a diameter of EQPC.

$$V_S = (\pi/6) \times (EQPC)^3 \times N_S,$$

wherein $N_S$ is the number of spherical particles in the sample, and EQPC is a median EQPC corresponding to the 50% cumulative value on the number-based cumulative particle diameter distribution curve of spherical particles.

The volume of the particles satisfying the definition S1 and the volume of the particles satisfying the definition S2 are calculated in accordance with the above equation, respectively, and a sum of these volumes means the volume of the spherical particles of L-HPC.

The volume fraction of each type of particles of L-HPC may be calculated from the following corresponding equation on basis of the above defined volumes, $V_m$, $V_{LF}$, $V_{SF}$ and $V_S$.

Volume fraction of fine particles=$\{V_m/(V_m+V_{LF}+V_{SF}+V_S)\}\times 100$

Volume fraction of long fibrous particles=$\{V_{LF}/(V_m+V_{LF}+V_{SF}+V_S)\}\times 100$ Volume fraction of short fibrous particles=$\{V_{SF}/(V_m+V_{LF}+V_{SF}+V_S)\}\times 100$ Volume fraction of spherical particles=$\{V_S/(V_m+V_{LF}+V_{SF}+V_S)\}\times 100$ The volume fraction of each type of particles, which are long fibrous particles, short fibrous particles, spherical particles and fine particles, is determined as follows. A dynamic image analysis type particle diameter distribution analyzer QICPIC/R16 (manufactured by Sympatec GmbH) equipped with a quantitative feeder VIBRI/L, an air flow type disperser RODOS/L and an M7 lens is used under the conditions of a frame rate of 500 Hz, an injector of 4 mm, a dispersion pressure of 1 bar. The graphics of the imaged particles are analyzed by analysis soft WINDOX5 Version: median EQPC of the number bases of various particles analyzed by 5.9.1.1 to determine the number-based median EQPC, the number-based median LEFI, the number-based median DIFI, the elongation, the aspect ratio and the circularity with respect to each type of particles. The volume fraction of each type of particles is calculated by the above equation based on the measured values. It is noted that M7 is used as the division of analysis.

(2) Method for Producing L-HPC to be Sieved in the First Sieving Step

First, there is described a method for producing L-HPC having a hydroxypropoxy group content of 5.0 to 16.0% by mass, which will be subjected to sieving in the first sieving step (hereinafter, also referred to as "starting L-HPC for sieving").

The L-HPC having a hydroxypropoxy group content of 5.0 to 16.0% by mass, which will be subjected to sieving in the first sieving step, may be produced, for example, by the method comprising steps of: bringing pulp into contact with an alkali metal hydroxide solution to obtain alkali cellulose, reacting the alkali cellulose with propylene oxide to obtain a reaction product mixture containing L-HPC, mixing the reaction product mixture, water and acid to obtain a precipitate, and washing, drying and pulverizing the precipitate.

First, the step of bringing pulp into contact with an alkali metal hydroxide solution to obtain alkali cellulose is described.

Examples of the pulp include pulp derived from wood, and pulp derived from cotton linter. Examples of the shape of the pulp include sheet, chips and powder.

Examples of the alkali metal hydroxide include sodium hydroxide and potassium hydroxide. The alkali metal hydroxide is preferably sodium hydroxide from the viewpoint of economy. As the alkali metal hydroxide solution, an aqueous solution of alkali metal hydroxide is preferable. The concentration of the alkali metal hydroxide in the aqueous alkali metal hydroxide solution is preferably from 20 to 50% by mass from the viewpoint of uniformity of the alkali cellulose and reaction efficiency.

The alkali cellulose may be optionally subjected to compression to obtain alkali cellulose containing a desired amount of alkali metal hydroxide after bringing pulp into contact with an alkali metal hydroxide solution. The alkali metal hydroxide content in the alkali cellulose is preferably from 15 to 35% by mass from the viewpoint of the reaction efficiency with propylene oxide. The alkali metal hydroxide content in the alkali cellulose may be measured by neutralization titration of the alkali cellulose with an acid (e.g. sulfuric acid) having a known concentration.

Next, the step of reacting the alkaline cellulose with propylene oxide to obtain a reaction product mixture containing L-HPC is described.

From the viewpoint of reaction controllability, it is preferable to carry out the reaction in a rotation type reactor, a pressure vessel with an internal stirrer, or the like, which is preferably capable of adjusting an internal temperature by a jacket. It is noted that the term "rotation type reactor" refers to a reactor in which a stirring effect is obtained by rotating the reactor itself. The amount of propylene oxide to be used is preferably from 1.0 to 20.0 parts by mass relative to 100 parts by mass of alkaline cellulose from the viewpoint of reaction efficiency of propylene oxide. The propylene oxide may be added after alkaline cellulose is heated to 30 to 60° C.

The reaction temperature is preferably from 40° C. to 80° C. from the viewpoint of reaction controllability and productivity. The reaction time is preferably from 0.5 to 6 hours from the viewpoint of reaction controllability and productivity.

Next, the step of mixing the reaction product mixture, water and an acid to obtain a precipitate is described.

The mixing may be carried out, for example, using a jacketed twin-shaft kneader.

The temperature of water is preferably from 10 to 50° C. from the viewpoint of solubility of the reaction product mixture. The amount of water to be used is preferably from 100 to 1000 parts by mass relative to 100 parts by mass of the alkali cellulose from the viewpoint of solubility of the reaction product mixture. It is noted that the amount of water may be mixed (e.g. added) at once, or may be divided and mixed (e.g. added) two or more times.

Examples of the acid include acetic acid and hydrogen chloride. An amount of the acid is preferably from 95 to 100% of the equivalent of the alkali metal hydroxide contained in the alkali cellulose from the viewpoint of reducing the amount of the alkali metal hydroxide remaining in L-HPC. The acid may be used as it is or may be used as a mixture with water. The acid is preferably used as a mixture of the acid and water from the viewpoint of avoiding a local neutralization reaction between the reaction product mixture and the acid.

In a preferred embodiment, the reaction product mixture is mixed with acid-containing water, wherein the acid is in amount of preferably from 5 to 80%, more preferably from 10 to 60%, and still more preferably from 10 to 40% of the equivalent required to neutralize the alkali metal hydroxide contained in the alkali cellulose so as to dissolve a portion of the reaction product mixture. The acid is further added up to an amount of the equivalent required to neutralize the alkali metal hydroxide contained in the alkaline cellulose so as to obtain crude L-HPC as a precipitate.

The mixing temperature is preferably from 5 to 80° C. from the viewpoint of solubility of the reaction product mixture. The mixing temperature may be controlled by a jacket temperature. The mixing time is preferably from 0.1 to 2 hours from the viewpoint of productivity.

Next, there are described the steps of washing, drying and pulverizing the precipitate to obtain L-HPC having a hydroxypropoxy group content of 5.0 to 16.0% by mass, which will be subjected to sieving.

The step of washing may comprise steps of, for example, bringing the precipitate into contact with water to obtain a mixture and dehydrating the mixture with a dehydrator. The temperature of water to be used for washing is 90° C. or higher from the viewpoint of washability. The amount of water to be used is preferably from 1000 to 5000 parts by mass relative to 100 parts by mass of alkali cellulose from the viewpoint of economy.

Examples of the dehydrator include a batch type centrifuge. The centrifugal effect of the dehydrator may be selected for sufficient dehydration. The centrifugal effect is preferably 500 G or more from the viewpoint of productivity.

The step of drying may be carried out, for example, by using a dryer. Examples of the dryer include a shelf dryer. The drying temperature is from 60 to 120° C. from the viewpoint of drying efficiency. The drying time is from 3 to 24 hours from the viewpoint of productivity.

The step of pulverizing may be carried out, for example, by using a pulverizer. Examples of the pulverizer preferably include an impact type pulverizer such as a hammer mill and an impact mill. The screen diameter in the pulverizer is preferably from 0.1 mm to 5.0 mm from the viewpoint of the particle diameter of L-HPC. Further optional drying may be carried out after the pulverization so that water content of pulverized L-HPC may be adjusted before sieving.

The water content of L-HPC to be sieved is preferably from 1.0 to 8.0% by mass, more preferably from 1.5 to 5.0% by mass, from the viewpoint of prevention of static charge in the sieving step. The water content of L-HPC to be sieved may be measured in accordance with "2.41 Loss on Drying Test" of General Tests cited in "Low-Substituted Hydroxypropyl Cellulose" in the Japanese Pharmacopoeia Seventeenth Edition.

The hydroxypropoxy group content of L-HPC to be sieved is 5.0 to 16.0% by mass, preferably 6.0 to 15.0% by mass, and more preferably 7.0 to 14.0% by mass. The hydroxypropoxy group content of L-HPC to be sieved may be measured by the quantitative method described in "Low-Substituted Hydroxypropyl Cellulose" of the Japanese Pharmacopoeia Seventeenth Edition.

The volume-based average particle diameter by the dry laser diffractometry of starting L-HPC to be sieved is from 10.0 to 90.0 μm, more preferably from 30.0 to 85.0 μm, still more preferably from 40.0 to 75.0 μm, particularly more preferably from 50.0 to 70.0 μm, from the viewpoint of the disintegrability, moldability (bindability) and flowability of L-HPC. The volume-based average particle diameter by the dry laser diffractometry of starting L-HPC to be sieved is measured in a dry method by using a laser diffraction particle diameter distribution analyzer Mastersizer 3000 (produced by Malvern Panalytical Ltd.) with Fraunhofer diffraction theory under the conditions of a dispersion pressure of 2 bar and the scattering intensity of 2 to 10%, as the diameter corresponding to 50% cumulative value on the volume-based cumulative particle size distribution curve.

The volume fraction of long fibrous particles of starting L-HPC to be sieved is preferably from 10.0 to 50.0%, more preferably from 10.5 to 45.0%, and still more preferably from 11.0 to 25.0%, from the viewpoint of good flowability, high moldability (bindability) and anti-capping performance of L-HPC.

The volume fraction of short fibrous particles of starting L-HPC to be sieved is preferably from 20.0 to 40.0%, more preferably from 22.5 to 35.0%, and still more preferably from 23.0 to 35.0%, from the viewpoint of good flowability, high moldability (bindability) and anti-capping performance of L-HPC.

The volume fraction of spherical particles of starting L-HPC to be sieved is preferably from 10.0 to 60.0%, more preferably from 15.0 to 59.0%, and still more preferably from 45.0 to 55.0%, from the viewpoint of good flowability and anti-capping performance of L-HPC.

The volume fraction of fine particles of starting L-HPC to be sieved is preferably from 0.0 to 10.0%, more preferably from 0.1 to 5.0%, and still more preferably from 1.0 to 3.5%, from the viewpoint of good flowability of L-HPC.

The angle of repose of starting L-HPC to be sieved is measured with using a powder tester PT-S type (produced by Hosokawa Micron Corporation) by the method (injection method) comprising steps of supplying powder onto a circular table having a diameter of 80 mm through the funnel until the angle of the powder deposition layer, which is the slope angle of the powder relative to the horizontal plane of the table, becomes constant, and measuring the constant angle.

A loose bulk density of starting L-HPC to be sieved is preferably less than 0.340 g/ml, more preferably from 0.150 to 0.335 g/ml. However, there is room for improvement in terms of flowablility of L-HPC. A tapped bulk density of starting L-HPC to be sieved is preferably less than 0.515 g/ml, more preferably from 0.250 to 0.510 g/ml. However, them is room for improvement in terms of flowability of L-HPC.

The degree of compaction of starting L-HPC to be sieved is preferably 33.0% or more, more preferably from 33.5 to 45.0%, and still more preferably from 33.5 to 35.0%. However, there is room for improvement in terms of flowability of L-HPC.

The "Loosened bulk density" refers to a bulk density in a loosely packed state, and is measured by uniformly supplying a sample through a sieve having mesh opening of 1 mm into a stainless steel cylindrical container having a diameter of 5.05 cm and a height of 5.05 cm (volume: 100 ml) from 23 cm above the container by using a powder tester PT-S type (produced by Hosokawa Micron Corporation), and leveling the supplied sample at the top face of the container for weighing.

The "tapped bulk density" is a bulk density in the state where a sample is closely packed into the cylindrical container by tapping. The term "tapping" is an operation in which a container filled with a sample is repeatedly dropped from a predetermined height to apply a light impact to the bottom of the container, thereby closely packing the sample in the container. In practice, after the "loose bulk density" is measured by supplying a sample into the container and leveling the supplied sample at the top face of the container for weighing, the container is capped at the top of the container, then filled with the sample up to the upper edge of the cap, and subjected to 180 times of tapping from a tap height of 1.8 cm. After the 180 times of tapping is completed, the cap is removed from the container, and then the sample is leveled at the top face of the container for weighing. The bulk density found in this state is considered as the tapped bulk density.

The "degree of compaction" is a value for indicating the degree of bulk density reduction, and is calculated by the following equation.

Degree of compaction (%)={(tapped bulk density−loose bulk density)/tapped bulk density}×100

(3) First Sieving Step Using Horizontal Movement

Next, there is described a first sieving step of sieving L-HPC having a hydroxypropoxy group content of 5 to 16% by mass with a sieve shaker with horizontal movement of a sieve surface to obtain a first sieve-residual L-HPC and a first sieve-passed L-HPC.

The horizontal movement allows coarse fibrous particles and spherical particles to be recovered as a residue on the sieve. The coarse fibrous particles deteriorate flowability, while the spherical particles do not deteriorate flowability.

The effective sieving area of the sieve to be used in the first sieving step is preferably from 0.0001 to 1,000 m$^2$, more preferably from 0.0010 to 100 m$^2$, from the viewpoint of industrial availability. The mesh opening of the sieve surface of the sieve to be used in the first sieving step may be appropriately selected depending on applications. The mesh opening is preferably from 0.045 to 0.500 mm, more preferably from 0.060 to 0.300 mm, from the viewpoint of the treatment rate or the flowability, disintegrability and bindability of L-HPC. The line diameter on the sieve surface of the sieve to be used in the first sieving step may be appropriately selected depending on applications. The line diameter is preferably from 0.001 to 5.0 mm, more preferably from 0.01 to 1.0 mm, from the viewpoint of strength. The number of installation stage of the sieve to be used in the first sieving step may be selected to be one or more. It is preferably from 1 to 10 stages, more preferably 1 stage, from the viewpoint of productivity.

When two or more stages of sieves having the same mesh openings are used, L-HPC having passed through all of the sieves may be used as the first sieve-passed L-HPC, and the residues on all of sieves may be combined and used as the first sieve-residual L-HPC. When two or more sieves having different mesh openings are used, L-HPC having passed through all of the sieves may be used as the first sieve-passed L-HPC. On the other hand, which residue or residues on the two or more sieves are used as the first sieve-residual L-HPC in the second sieving step may be determined, for example, based on the findings of the hydroxypropoxy group content, the average particle diameter, and/or the volume fractions of long fibrous particles, short fibrous particles, spherical particles and fine particles with respect to the residual L-HPC on each sieve. Further, the angle of repose, a loose bulk density, a tapped bulk density and/or the degree of compaction of the residual L-HPC on each sieve may be found to determine which residue or residues on the two or more sieves are used as the first sieve-residual L-HPC in the second sieving step. More specifically, the first-sieve residual low-substituted hydroxypropyl cellulose is selected to have a volume fraction of short fibrous particles of less than 20% relative to all of particles which are classified into fine particles, spherical particles, long fibrous particles and the short fibrous particles based on a dynamic image analysis; wherein the fine particles have a length of fiber of less than 40 μm; the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EQPC}$) of a circle that has the same area as a projection area of a particle to a real perimeter Pa of a particle, of 0.7 or more; the long fibrous particles have a length of fiber of 200 μm or more, an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; the short fibrous particles have a length of fiber of 40 μm or more and less than 200 μm and an elongation of less than 0.5, and consist of first and second short fibrous particles, wherein the first fibrous particles have an aspect ratio of less than 0.5 and the second short fibrous particles have an aspect ratio of 0.5 or more and a circularity of less than 0.7. Further, the first sieve-residual low-substituted hydroxypropyl cellulose is preferably selected to have an average particle diameter of more than 90.0 μm and not more than 300.0 μm by combining some or all of the residues on the two or more sieves.

The horizontal movement of the sieve surface includes turning movement of the sieve surface, and a vibrating movement of the sieve surface in the horizontal direction.

Examples of the sieve shaker with turning movement of a sieve surface to be used in the first sieving step include an in-plane motion sieving machine and a Row-Tap type sieving machine. Examples of the in-plane motion sieving machine include an aluminum square sifter (produced by Meiji Machine Co., Ltd.), a plan sifter (produced by Meiji Machine Co., Ltd.), a gyratory sifter (produced by Meiji Machine Co., Ltd.), a gyro sifter (produced by TOKUJU CORPORATION), a ROTEX screener (produced by ROTEX Co., Ltd.), and an Allgaier sifter (produced by Allgaier Co., Ltd.). Examples of the Ro-Tap type sieving machine include a Ro-Tap type sieving shaker (produced by TAKEDA Corporation and Kansai Wire Netting Co., Ltd.), and a BS sieve shaker (produced by SEISHIN ENTERPRISE Co., Ltd.).

The sieving conditions for the sieving shaker with turning movement of a sieve surface in the first sieving step may be appropriately selected depending on a type of the sieving shaker and/or the intended particle size distribution of L-HPC. The number of rotations in the in-plane sieving machine and the Ro-Tap type sieving shaker is preferably from 10 to 500 rpm from the viewpoint of efficient sieving. The radius of rotation in the in-plane motion sieving machine and the Ro-Tap type sieving shaker is preferably from 5 to 100 mm from the standpoint of efficient sieving.

The sieving time in the first sieving step, that is, the time from the start to the end of sieving L-HPC, is preferably 0.1 to 12 hours from the viewpoint of productivity.

The water content of the first sieve-residual L-HPC is preferably from 1.00 to 8.00% by mass, more preferably from 1.50 to 5.00% by mass, from the viewpoint of prevention of static charge in the sieving step.

The hydroxypropoxy group content of the first sieve-residual L-HPC is from 5.0 to 16.0% by mass, preferably from 6.0 to 15.0% by mass, and more preferably from 7.0 to 14.0% by mass.

The volume-based average particle diameter by the dry laser diffractometry of the first sieve-residual L-HPC is preferably more than 90.0 μm and not more than 300.0 μm, more preferably from 95.0 to and 150.0 μm. However, there is room for improvement in terms of moldability (bindability) and flowability of L-HPC.

The volume fraction of long fibrous particles in the first sieve-residual L-HPC is preferably from 10.0 to 50.0%, more preferably from 10.5 to 45.0%, from the viewpoint of good flowability and high moldability (bindability) and anti-capping performance of L-HPC.

The volume fraction of short fibrous particles in the first sieve-residual L-HPC is preferably from 0.0 to less than 20.0%, more preferably from 0.0 to 10.0%, and still more preferably from 0.0 to 5.0%. However, there is room for improvement in terms of good flowability, high moldability (bindability) and anti-capping performance of L-HPC.

The volume fraction of spherical particles in the first sieve-residual L-HPC is preferably from 10.0 to 60.0%, more preferably from 15.0 to 59.0%, and still more preferably from 45.0 to 55.0%, from the viewpoint of good flowability and anti-capping performance of L-HPC.

The volume fraction of fine particles in the first-sieve residual L-HPC is preferably from 0.0 to 10.0%, more preferably from 0.1 to 5.0%, and still more preferably from 0.2 to 3.5%, from the viewpoint of good flowability of L-HPC.

The loose bulk density of the first sieve-residual L-HPC is preferably less than 0.340 g/ml, more preferably from 0.150 to 0.335 g/ml, and still more preferably from 0.160 to 0.200 g/ml. However, there is room for improvement in terms of flowability of L-HPC.

The tapped bulk density of the first sieve-residual L-HPC is preferably less than 0.515 g/ml, more preferably from 0.250 to 0.510 g/ml, and still more preferably from 0.250 to 0.350 g/ml. However, there is room for improvement in terms of flowability of L-HPC.

The degree of compaction of the first sieve-residual L-HPC is preferably 33.0% or more, more preferably from 33.5 to 45.0%, from the viewpoint of flowability of L-HPC. However, there is room for improvement in terms of flowability of L-HPC.

Regarding the first sieve-residual L-HPC, a water content, a hydroxypropoxy group content, a volume fraction of long fibrous particles, a volume fraction of short fibrous particles, a volume fraction of spherical particles, a volume fraction of fine particles, a loose bulk density, a tapped bulk density, and the degree of compaction may be determined in the same manner as those of the starting L-HPC.

(4) Second Sieving Step Using Vertical Motion

Next, there is described a second sieving step of sieving the first sieve-residual L-HPC with a sieve shaker with vertical movement of a sieve surface to obtain second sieve-residual L-HPC and second sieve-passed L-HPC.

The vertical movement allows coarse fibrous particles which deteriorate flowability to be separated as a second sieve-passed fraction, while leaving L-HPC having target physical properties on the second sieve.

The effective sieve area of the sieve to be used in the second sieving step is preferably from 0.0001 to 1,000 m$^2$, more preferably from 0.0010 to 100 m$^2$, from the viewpoint of industrial availability. The mesh opening of the sieve surface of the sieve to be used in the second sieving step may be appropriately selected depending on applications. The mesh opening is preferably from 0.045 to 0.500 mm, more preferably from 0.060 to 0.300 mm, from the viewpoint of the treatment rate, the flowability, the disintegrability and the bindability of L-HPC. The mesh opening of the sieve surface of the sieve to be used in the second sieving step is preferably the same as the mesh opening of the sieve surface of the sieve used in the first sieving step from the viewpoint of easy removal of unnecessary particles by the horizontal movement and the vertical movement. The line diameter on the sieve surface of the sieve to be used in the second sieving step may be appropriately selected depending on applications. The line diameter is preferably from 0.001 to 5.0 mm, more preferably from 0.01 to 1.0 mm, from the viewpoint of strength. The number of installation stages of the sieve in the second sieving step may be one or more stages. It is preferably from 1 to 10 stages, more preferably 1 stage, from the viewpoint of productivity.

In addition, when two or more stages of sieves having the same mesh opening are used, L-HPC having passed through all of the sieves is used as the second sieve-passed L-HPC, and the residues on the two more sieves may be combined and used as the second sieve-residual L-HPC. When two or more sieves having different mesh openings are used, L-HPC having passed through all of the sieves is used as the second sieve-passed L-HPC. On the other hand, which residue or residues on the sieves are used as the second sieve-residual L-HPC is determined based on the findings of a hydroxypropoxy group content, an average particle diameter, each volume fraction of long fibrous particles, short fibrous particles, spherical particles and fine particles, the angle of repose, a loose bulk density, a tapped bulk density and the degree of compaction of each L-HPC remaining on sieves.

The vertical movement of the sieve surface includes continuous vibrational movement and intermittent vibrational movement (impact movement) by a hammer or the like.

Examples of the sieving shaker having a sieve surface moving in a vertical direction to be used in the second sieving step include a vibration sieving machine, and a Ro-Tap type sieving machine equipped with a hammer. Examples of the vibration sieving machine include ripple flow K and R screens (produced by Kobukuro Techno Co., Ltd.), low head K and R screens (produced by Kobukuro Techno Co., Ltd.), electromagnetic screens (produced by Sinfonia Technology Co., Ltd.), electromagnetic labo sieving machine (produced by Fritsch GmbH), RV screens (produced by Sinfonia Technology Co., Ltd.), balanced screens (produced by Sinfonia Technology Co., Ltd.), BM screens (produced by Sinfonia Technology Co., Ltd.), wave screens (produced by Sinfonia Technology Co., Ltd.), linear drive screens (produced by Sinfonia Technology Co., Ltd.), gyro screens (produced by Sinfonia Technology Co., Ltd.), rubber spring screens (produced by Sinfonia Technology Co., Ltd.), a grizzly feeder (produced by Sinfonia Technology Co., Ltd.), and a circular vibration sieving machine (produced by Dalton Corporation). Examples of the Ro-Tap type sieving machine include a Ro-Tap type sieving shaker (produced by TAKEDA Corporation and Kansai Wire Netting Co., Ltd.), and a BS sieve shaker (produced by SEISHIN ENTERPRISE Co., Ltd.).

The Ro-Tap type sieving machine can have turn movement. The Ro-Tap type sieving machine without a hammer provides only horizontal movement (i.e., the turn movement), while the Ro-Tap type sieving machine equipped with a hammer provides a combination of the horizontal motion (i.e. the turn movement) and the vertical movement by impact.

The sieving conditions in the second sieving step may be appropriately selected depending on a type of the sieving machine and the intended particle diameter distribution of L-HPC. The frequency in the vibration sieving machine is preferably from 600 to 100,000 rpm from the viewpoint of efficient sieving. The amplitude in the vibration sieving machine is preferably from 0.1 to 100 mm from the viewpoint of efficient sieving. The weight phase angle in a round vibration sieving machine, which is one of the vibration sieving machines, is preferably 15 to 90 degrees, more preferably 35 to 90 degrees, from the viewpoint of efficient sieving.

The frequency of hammer strokes in the Ro-Tap type sieving machine is preferably 50 to 70 times per minute from the viewpoint of efficient sieving. Further, by using a sieve shaker, such as a Ro-Tap type sieving shaker (produced by TAKEDA Corporation and Kansai Wire Netting Co., Ltd.) and a BS sieve shaker (SEISHIN ENTERPRISE Co., Ltd.), which can perform horizontal movement (e.g. turn movement) of the sieve surface in addition to the vertical movement of the sieve surface, the sieving may be carried out by applying both of the horizontal movement (e.g. turn movement) and the vertical movement to the sieve surface. The number of rotations in the Ro-Tap type sieving machine is preferably from 10 to 500 rpm from the viewpoint of efficient sieving. The radius of rotation in the Ro-Tap type sieving machine is preferably from 10 to 100 mm from the viewpoint of efficient sieving.

The sieving time in the second sieving step, that is, the time from the start of the feeding of the first sieve-residual L-HPC to the end of the sieving, is preferably from 0.1 to 12 hours from the viewpoint of productivity.

Next, there is described a step of combining the first sieve-passed L-HPC and the second sieve-residual L-HPC to obtain the sieved L-HPC.

The step of combining the first sieve-passed L-HPC and the second sieve-residual L-HPC is preferably carried out by mixing both. The mixing of the first sieve-passed L-HPC and the second sieve-residual L-HPC is not particularly limited as long as it can be sufficiently mixed. The mixing may be carried out by using, for example, a mixer. Examples of the mixer include a rotary mixer, a mechanical stirring mixer, a flow stirring mixer, a non-stirring mixer, and a high-speed and high-shear impact mixer.

The hydroxypropoxy group content of the sieved L-HPC is preferably from 5.0 to 16.0% by mass, more preferably from 6.0 to 15.0% by mass, and still more preferably from 7.0 to 14.0% by mass. When the hydroxypropoxy group content is less than 5.0% by mass, the water swelling after water absorption of L-HPC becomes low. When the hydroxypropoxy group content is more than 16.0% by mass, the water solubility of L-HPC becomes large so that the disintegrability becomes insufficient when used in a solid preparation.

The volume-based average particle diameter by the dry laser diffractometry of the sieved L-HPC is preferably from 10.0 to 90.0 μm, more preferably from 30.0 to 85.0 μm, still more preferably from 40.0 to 75.0 μm, particularly preferably from 50.0 to 70.0 μm, from the viewpoint of the disintegrability, moldability (bindability) and flowability of L-HPC.

The volume fraction of long fibrous particles in the sieved L-HPC is preferably from 10.0 to 50.0%, more preferably from 10.5 to 45.0%, and still more preferably from 11.0 to 20.0%, from the viewpoint of good flowability and high moldability (bindability) and anti-capping performance of L-HPC.

The volume fraction of short fibrous particles in the sieved L-HPC is preferably from 20.0 to 40.0%, more preferably from 22.5 to 35.0%, and still more preferably from 23.0 to 35.0%, from the viewpoint of good flowability, high moldability (bindability) and anti-capping performance of L-HPC.

The volume fraction of spherical particles in the sieved L-HPC is preferably from 10.0 to 60.0%, more preferably from 15.0 to 59.0%, and still more preferably from 45.0 to 58.0%, from the viewpoint of good flowability and anti-capping performance of L-HPC.

The volume fraction of fine particles in the sieved L-HPC is preferably from 0.0 to 10.0%, more preferably from 0.1 to 5.0%, and still more preferably from 1.0 to 3.5%, from the viewpoint of good flowability of L-HPC.

The loose bulk density of the sieved L-HPC is preferably 0.340 g/ml or more, more preferably from 0.345 to 0.600 g/ml, and still more preferably from 0.350 to 0.400 g/ml, from the viewpoint of flowability of L-HPC.

The tapped bulk density of the sieved L-HPC is preferably 0.515 g/ml or more, more preferably from 0.520 to 1.000 g/ml, and still more preferably from 0.525 to 0.600 g/ml, from the viewpoint of flowability of L-HPC.

The degree of compression of the sieved L-HPC is preferably less than 33.0%, more preferably from 1.0 to 32.5%, and still more preferably from 25.0 to 32.0%, from the viewpoint of flowability of L-HPC.

A hydroxypropoxy group content, a volume fraction of long fibrous particles, a volume fraction of short fibrous particles, a volume fraction of spherical particles, a volume fraction of fine particles, a loose bulk density, a tapped bulk density and the degree of compression of the sieved L-HPC may be determined in the same manner as the determination of those of starting L-HPC to be sieved in the first sieving step.

EXAMPLES

The invention will be described in detail with reference to Examples and Comparative Examples. It should not be construed that the invention is limited to or by Examples.

Example 1 (Turn Movement Ro-Tap Type Sieving Machine and Vibration Sieving Machine)

Pulp sheet derived from wood was immersed in a 43% by mass aqueous sodium hydroxide solution, and pressed to obtain alkali cellulose containing 22% by mass of sodium hydroxide. Next, 100 parts by mass of the alkali cellulose was placed in a rotary reactor having an internal volume 5 L, and the inside of the rotary reactor was substituted with nitrogen. Then the rotary reactor was placed in a hot water bath of 50° C., and rotated until the internal temperature became 40° C. Then, the inside of the rotary reactor was reduced in pressure, and 11.6 parts by mass of propylene oxide was added thereto. The resulting mixture was reacted at an internal temperature of 50° C. for 2 hours and 30 minutes while rotating, thereby obtaining a reaction product mixture containing 108 parts by mass of L-HPC.

The reaction product mixture containing L-HPC was added to a mixture of 230 parts by mass of hot water of 35° C. (relative to 100 parts by mass of the alkaline cellulose) and 11.9 parts by mass of acetic acid (36% of the neutralization equivalent of sodium hydroxide contained in the alkaline cellulose) in a jacketed biaxial kneader, and kneaded at a jacket temperature of 35° C. for 40 minutes to dissolve a part of L-HPC. Then, 64.0 parts by mass of a 33% by mass aqueous acetic acid solution (relative to 100 parts by mass of the alkali cellulose; and 64% of the neutralization equivalent of sodium hydroxide contained in the alkaline cellulose) was added thereto and mixed at a jacket temperature of 35° C. for 10 minutes to obtain 413.9 parts by mass of a neutralized product. Next, the neutralized product was dispersed in 3000 parts by mass of hot water of about 90° C. (relative to 100 parts by mass of the alkali cellulose), dehydrated using a batch-type centrifuge (H-130A produced by KOKUSAN Co., Ltd.) at the centrifugal effect of 1258 G, and then dried using a shelf dryer (DKN-402 produced by Yamato Scientific Co., Ltd.) at 80° C. for 18 hours. Then, the dried product was pulverized with an impact type pulverizer (impact mill: victory mill VP-1 produced by Hosokawa Micron Corporation; a screen diameter of 0.5 mm), and then re-pulverized with the impact type pulverizer having the screen diameter changed to 0.3 mm. The re-pulverized product was dried at 80° C. for 3 hours to obtain starting L-HPC to be sieved in the first sieving step.

Regarding the obtained starting L-HPC to be sieved, a water content, a hydroxypropoxy group content, an average particle diameter, each volume fraction of long fibrous particles, short fibrous particles, spherical particles and fine particles, a loose bulk density, a tapped bulk density and the degree of compaction were measured. The results are shown in Table 1.

Subsequently, 100 g of the obtained starting L-HPC to be sieved was supplied to a rotary sieving shaker (produced by TAKEDA Corporation) in which a 200 mesh sieve (an effective sieve area of 0.0314 m$^2$, mesh opening of 0.075 mm, a wire diameter of 0.05 mm, and produced by Kansai Wire Netting Co., Ltd.) was installed in one stage. The sieving with turn movement of a sieve surface was operated under the conditions of a rotational speed of 250 rpm, a rotational radius of 50 mm and a sieving time of 10 minutes without hammer strokes, thereby obtaining 25.8 g of the first sieve-residual L-HPC and 74.2 g of the first sieve-passed L-HPC.

Then, 25.8 g of the first sieve-residual L-HPC was supplied to an electromagnetic labo sieving shaker A-3PRO (produced by Fritsch GmbH) in which a 200 mesh sieve (an effective sieve area of 0.0314 m$^2$, mesh opening of 0.075 mm, a wire diameter of 0.05 mm, produced by Kansai Wire Netting Co., Ltd.) was installed one stage. The sieve with vertical vibration movement of a sieve surface was operated under the conditions of a frequency of 3000 rpm, an amplitude of 1 mm, and sieving time of 10 minutes, thereby obtaining 17.5 g of the second sieve-residual L-HPC and 8.3 g of the second sieve-passed L-HPC.

Then, the first sieve-passed L-HPC and the second sieve-residual L-HPC were mixed to obtain 91.7 g of sieved L-HPC.

Regarding the obtained sieved L-HPC, a hydroxypropoxy group content, an average particle diameter, each volume fraction of long fibrous particles, short fibrous particles, spherical particles and fine particles, the angle of repose, a loose bulk density, a tapped bulk density and the degree of compaction were measured. The results are shown in Table 1.

Example 2 (Turn Movement Ro-Tap Type Sieving Machine and Impact-Added Turn Movement Ro-Tap Type Sieving Machine)

The 100 g of starting L-HPC produced in the same manner as in EXAMPLE 1 was supplied to a Ro-Tap type sieve shaker (produced by TAKEDA Corporation) in which a 200 mesh sieve (an effective sieve area of 0.0314 m$^2$, mesh opening of 0.075 mm, a wire diameter of 0.05 mm, and produced by Kansai Wire Netting Co., Ltd.) was installed in one stage. The sieve with turn movement of a sieve surface without hammer strokes was operated under the conditions of a rotational speed of 250 rpm, a rotational radius of 50 mm, and sieve time of 10 minutes, thereby obtaining 25.8 g of the first sieve-residual L-HPC to be sieved in the second sieving step and 74.2 g of the first sieve-passed L-HPC to be combined with the second sieve-residual L-HPC.

Subsequently, 25.8 g of the first sieve-residual L-HPC to be used in the second sieving step was supplied to a Ro-Tap type sieving shaker (produced by TAKEDA Corporation) in which a 200 mesh sieve (an effective sieve area of 0.0314 m$^2$, mesh opening of 0.075 mm, a wire diameter of 0.05 mm, produced by Kansai Wire Netting Co., Ltd.) was installed in one stage. The sieve with turn movement and vertical movement by hammer strokes of a sieve surface was operated under the conditions of a rotational speed of 250 rpm, a shaking width of 50 mm, hammer strokes of 67 times/min and sieve time of 10 minutes, thereby obtaining 17.2 g of the second sieve-residual L-HPC and 8.6 g of the second sieve-passed L-HPC.

Then, the first sieve-passed L-HPC and the second sieve-residual L-HPC were mixed to obtain 91.4 g of sieved L-HPC.

Regarding the obtained sieved L-HPC, a hydroxypropoxy group content, an average particle diameter, each volume fraction of long fibrous particles, short fibrous particles, spherical particles and fine particles, a loose bulk density, a tapped bulk density and the degree of compaction were measured in the same manner as in Example 1. The results are shown in Table 1.

Comparative Example 1 (Turn Movement Ro-Tap Type Sieving Machine)

The 100 g of starting L-HPC produced in the same manner as in Example 1 was supplied to a Ro-Tap type sieving shaker (produced by TAKEDA Corporation) in which the same sieve as in Example 1 was installed in one stage. The sieve with turn movement of a sieve surface was operated under the conditions of a rotational speed of 250 rpm, a rotational radius of 50 mm, and sieve time of 10 minutes without hammer strokes, thereby obtaining 25.8 g of the sieve-residual L-HPC and 74.2 g of the sieve-passed L-HPC.

Regarding the sieve-passed L-HPC, a hydroxypropoxy group content, an average particle diameter, each volume fraction of long fibrous particles, short fibrous particles, spherical particles and fine particles, a loose bulk density, a tapped bulk density and the degree of compaction were measured in the same manner as in Example 1. The results are shown in Table 1.

Comparative Example 2 (Impact-Added Turn Movement Ro-Tap Type Sieving Machine)

The 100 g of the starting L-HPC produced in the same manner as in Example 1 was supplied to a Ro-Tap type sieving shaker (produced by TAKEDA Corporation) in which the same sieve as in Example 1 was installed in one stage. The sieve with turn movement and vertical movement by hammer strokes of a sieve surface was operated under the conditions of a rotational speed of 250 rpm, a shaking width of 50 mm, hammer strokes of 67 times/minute, and sieve time of 10 minutes, thereby obtaining 20.0 g of the sieve-residual L-HPC and 80.0 g of the sieve-passed L-HPC80.0 g.

Regarding the sieve-passed L-HPC, a hydroxypropoxy group content, a average particle diameter, each volume fraction of long fibrous particles, short fibrous particles, spherical particles and fine particles, a loose bulk density, a tapped bulk density and the degree of compaction were measured in the same manner as in Example 1. The results are shown in Table 1.

<Evaluation of Tablet Properties>

(1) Preparation of Drug-Containing Granules for Tableting

The 490 g of acetaminophen fine powder (produced by Yamamoto Chemical Co., Ltd.) was placed in a fluidized bed granulator Multiplex MP-01 (produced by Powrex Corporation), and granulated, while spraying 200 g of a 5% by mass aqueous solution of hydroxypropyl methyl cellulose (hydroxypropoxy group content of 8.8% by mass, methoxy group content of 29.0% by mass, and viscosity at 20° C. of 3.0 mPa·s as determined in a 2% by mass aqueous solution)

thereto, under the following conditions: an intake air temperature of 60° C., an air flow of 0.5 to 0.7 m³/min, an exhaust gas temperature of 30 to 35° C., a spray air pressure of 200 kPa, and a spray rate of 10 g/min.

Subsequently, the granulation product was dried until the exhaust gas temperature became 45° C., and then passed through a sieve having mesh opening of 500 μm to obtain granules containing 98% by mass of acetaminophen.

(2) Production of Tablets

The 90 parts by mass of acetaminophen-containing granules and 10 parts by mass of each L-HPC produced in Examples and Comparative Examples were mixed to obtain a mixture of the acetaminophen-containing granules and L-HPC. Next, 100 parts by mass of the mixture of acetaminophen-containing granules and L-HPC was mixed with 0.5 parts by mass of magnesium stearate as a lubricant, and tableted with a rotary tableting machine VIRGO (produced by Kikusui Seisakusho Ltd.) at a tableting pressure of 12.5 kN (about 249 MPa) and a tableting rate of 20 rpm to produce each tablet having diameter of 8 mm, a radius of curvature of 12 mm, and tablet mass of 200 mg.

(3) Evaluation of Capping Occurrence Ratio

The capping occurrence ratio of the tablets was obtained by placing 50 tablets in a drum of a friability tester TA (produced by ERWEKA GmbH); rotating the drum at 25 rpm 250 times for 10 minutes; and then counting the number of tablets in which capping occurred, that is, counting the number of tablets having division into two layers, for calculating the capping occurrence ratio by the following formula.

Capping occurrence ratio (%)={(number of tablets having capping occurred)/50}×100

The results are shown in Table 1.

(4) Evaluation of Tablet Hardness

The hardness of tablet was measured as the maximum breaking strength when the tablet was broken by applying a load at a rate of 1 mm/sec in the diameter direction of the tablet using a tablet hardness tester TBH-125 (produced by ERWEKA GmbH).

(5) Evaluation of Disintegration Time

The disintegration time of tablet was measured using a tablet disintegration tester (NH-1HM type, produced by Toyama Sangyo Co., Ltd.) in accordance with the disintegration test method (test solution: water, without disks) of the Japanese Pharmacopeia Seventeenth Edition.

TABLE 1

| | | | Example 1 | Example 2 | Comp.Ex. 1 | Comp.Ex. 2 |
|---|---|---|---|---|---|---|
| L-HPC to be sieved in first sieving step | water content | % | 3.3 | 3.3 | 3.3 | 3.3 |
| | HPO content | % | 11.2 | 11.2 | 11.2 | 11.2 |
| | average particle diameter | μm | 62.0 | 62.0 | 62.0 | 62.0 |
| | long fibrous particles | % | 20.7 | 20.7 | 20.7 | 20.7 |
| | short fibrous particles | % | 25.0 | 25.0 | 25.0 | 25.0 |
| | spherical particles | % | 51.2 | 51.2 | 51.2 | 51.2 |
| | fine particles | % | 3.1 | 3.1 | 3.1 | 3.1 |
| | loose bulk density | g/ml | 0.334 | 0.334 | 0.334 | 0.334 |
| | tapped bulk density | g/ml | 0.505 | 0.505 | 0.505 | 0.505 |
| | degree of compaction | % | 33.9 | 33.9 | 33.9 | 33.9 |
| first sieving step | movement on sieve surface | type | turning | turning | turning | turning and impact |
| | mass of first sieve-residual L-HPC | g | 25.8 | 25.8 | 25.8 | 20.0 |
| | yield of first sieve-residual L-HPC | % | 25.8 | 25.8 | 25.8 | 20.0 |
| | mass of first sieve-passed L-HPC | g | 74.2 | 74.2 | 74.2 | 80.0 |
| | yield of first sieve-passed L-HPC | % | 74.2 | 74.2 | 74.2 | 80.0 |
| first sieve-residual L-HPC | water content | % | 3.3 | 3.3 | — | — |
| | HPO content | % | 11.2 | 11.2 | — | — |
| | average particle diameter | μm | 124.0 | 124.0 | — | — |
| | long fibrous particles | % | 44.7 | 44.7 | — | — |
| | short fibrous particles | % | 3.4 | 3.4 | — | — |
| | spherical particles | % | 51.7 | 51.7 | — | — |
| | fine particles | % | 0.3 | 0.3 | — | — |
| | loose bulk density | g/ml | 0.175 | 0.175 | — | — |
| | tapped bulk density | g/ml | 0.314 | 0.314 | — | — |
| | degree of compaction | % | 44.2 | 44.2 | — | — |
| second sieving step | movement on sieve surface | type | vibration | turning and impact | — | — |
| | mass of second sieve-residual L-HPC | g | 17.5 | 17.2 | — | — |
| | yield of second sieve-residual L-HPC | % | 17.5 | 17.2 | — | — |
| | mass of second sieve-passed L-HPC | g | 8.3 | 8.6 | — | — |
| | yield of second sieve-passed L-HPC | % | 8.3 | 8.6 | — | — |
| combination of first sieve-passed L-HPC and second sieve-residual L-HPC | yield | % | 91.7 | 91.4 | 74.2 | 80.0 |
| | HPO content | % | 11.2 | 11.2 | 11.2 | 11.2 |
| | average particle diameter | μm | 63.6 | 63.7 | 53.8 | 53.7 |
| | long fibrous particles | % | 18.1 | 17.4 | 12.2 | 13.4 |
| | short fibrous particles | % | 25.2 | 25.9 | 28.3 | 27.6 |
| | spherical particles | % | 54.5 | 54.3 | 56.5 | 55.6 |
| | fine particles | % | 2.2 | 2.3 | 3.1 | 3.4 |
| | loose bulk density | g/ml | 0.373 | 0.377 | 0.369 | 0.367 |
| | tapped bulk density | g/ml | 0.539 | 0.541 | 0.538 | 0.535 |
| | degree of compaction | % | 30.8 | 30.4 | 31.4 | 31.5 |
| | capping occurrence ratio | % | 0 | 0 | 0 | 0 |
| | tablet hardness | N | 113 | 117 | 114 | 114 |
| | disintegration time | sec | 67.7 | 67.5 | 69.7 | 69.9 |

* "HPO" is an abbreviation of hydroxypropoxyl.

Comparing the results of Examples 1 to 2 with those of Comparative Examples 1 to 2, the yields were good and flowability (a loose bulk density, a tapped bulk density and the degree of compaction) was maintained in Examples 1 to 2 despite the fact that increase of the volume fraction of long fibrous particles which is considered to deteriorate the flowability, and decrease of the volume fraction of spherical particles and fine particles which are considered to enhance the flowability. In addition, the tablet properties (capping occurrence ratio, tablet hardness and disintegration time) also were good without compromise.

It is considered that sieving with a sieving shaker with horizontal movement of a sieve surface allows coarse fibrous particles and spherical particles to be recovered as the residues on the sieve, wherein the coarse fibrous particles deteriorate flowability, while the spherical particles do not deteriorate flowability; and then sieving of the residue on the sieve surface with a sieve shaker with vertical movement of a sieve surface allows the coarse fibrous particles which deteriorate flowability to be separated as a sieve-passed fraction. As a result, sieved L-HPC can be produced at high yield.

In addition, sieving only with a sieve shaker with horizontal movement of a sieve surface leaves L-HPC having target physical properties behind on the sieve surface as shown in Comparative Example 1. Consequently, the yield is unsatisfactory. On the other hand, sieving only with a sieving shaker with vertical movement and horizontal movement of a sieve surface allows coarse fibrous particles which deteriorate flowability to pass through the sieve, as shown in Comparative Example 2. Consequently, the yield of the target L-HPC in Comparative Example 2 is higher than the yield in Comparative Example 1, but lower than the yields in Examples 1 and 2.

The invention claimed is:

1. A method for producing sieved low-substituted hydroxypropyl cellulose comprising:
    providing low-substituted hydroxypropyl cellulose having a hydroxypropoxy group content of 5% to 16% by mass, a loose bulk density of 0.150 to 0.340 g/mL, and a tapped bulk density of 0.250 to 0.515 g/mL;
    a first sieving step of sieving the provided low-substituted hydroxypropyl cellulose with a sieve shaker with horizontal movement of a sieve surface to obtain first sieve-residual low-substituted hydroxypropyl cellulose and first sieve-passed low-substituted hydroxypropyl cellulose,
    a second sieving step of sieving the first sieve-residual low-substituted hydroxypropyl cellulose from the first sieving step with a sieve shaker with vertical movement of a sieve surface to obtain second sieve-residual low-substituted hydroxypropyl cellulose and second sieve-passed low-substituted hydroxypropyl cellulose, and
    combining the first sieve-passed low-substituted hydroxypropyl cellulose and the second sieve-residual low substituted hydroxypropyl cellulose in the absence of the second sieve-passed low substituted hydroxypropyl cellulose to obtain the sieved low-substituted hydroxypropyl cellulose,
    wherein the sieved low-substituted hydroxypropyl cellulose has a loose bulk density of 0.350 to 0.600 g/mL and a tapped bulk density of 0.525 to 1.000 g/mL.

2. The method for producing sieved low-substituted hydroxypropyl cellulose according to claim 1, wherein the low-substituted hydroxypropyl cellulose to be sieved in the first sieving step has a degree of compaction of 33.0% or more.

3. The method for producing sieved low-substituted hydroxypropyl cellulose according to claim 1, wherein the first sieve-residual low substituted hydroxypropyl cellulose is classified, based on a dynamic image analysis, into fine particles, spherical particles, long fibrous particles, and the short fibrous particles,
    wherein
        the fine particles have a length of fiber of less than 40 μm;
        the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EPQC}$) of a circle that has the same area as a projection area of a particle to areal perimeter ($P_{real}$) of a particle, of 0.7 or more;
        the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; and
        the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7,
    wherein the volume fraction of the short fibrous particles relative to the entirety of the first sieve-residual low-substituted hydroxypropyl cellulose is less than 20%.

4. The method for producing sieved low-substituted hydroxypropyl cellulose according to claim 1, wherein the first sieve-residual low-substituted hydroxypropyl cellulose has an average particle size of more than 90.0 μm and not more than 300.0 μm.

5. The method for producing sieved low-substituted hydroxypropyl cellulose according to claim 2, wherein the first sieve-residual low substituted hydroxypropyl cellulose is classified, based on a dynamic image analysis, into fine particles, spherical particles, long fibrous particles, and the short fibrous particles,
    wherein
        the fine particles have a length of fiber of less than 40 μm;
        the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EPQC}$) of a circle that has the same area as a projection area of a particle to areal perimeter ($P_{real}$) of a particle, of 0.7 or more;
        the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; and the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7, wherein the volume fraction of the short fibrous particles relative to the entirety of the first sieve-residual low-substituted hydroxypropyl cellulose is less than 20%.

6. The method for producing sieved low-substituted hydroxypropyl cellulose according to claim 2, wherein the first sieve-residual low-substituted hydroxypropyl cellulose has an average particle size of more than 90.0 μm and not more than 300.0 μm.

7. The method for producing sieved low-substituted hydroxypropyl cellulose according to claim 3, wherein the first sieve-residual low-substituted hydroxypropyl cellulose has an average particle size of more than 90.0 μm and not more than 300.0 μm.

8. The method for producing sieved low-substituted hydroxypropyl cellulose according to claim 5, wherein the first sieve-residual low-substituted hydroxypropyl cellulose has an average particle size of more than 90.0 μm and not more than 300.0 μm.

* * * * *

UNITED STATES PATENT AND TRADEMARK OFFICE
CERTIFICATE OF CORRECTION

| | |
|---|---|
| PATENT NO. | : 11,421,043 B2 |
| APPLICATION NO. | : 17/000836 |
| DATED | : August 23, 2022 |
| INVENTOR(S) | : Miki et al. |

It is certified that error appears in the above-identified patent and that said Letters Patent is hereby corrected as shown below:

In the Specification

Column 9, Line 61: delete "Pa" insert --$P_{real}$--

Signed and Sealed this
Ninth Day of May, 2023

Katherine Kelly Vidal
*Director of the United States Patent and Trademark Office*